(12) United States Patent
Pacetti et al.

(10) Patent No.: US 8,778,375 B2
(45) Date of Patent: Jul. 15, 2014

(54) AMORPHOUS POLY(D,L-LACTIDE) COATING

(75) Inventors: Stephen D. Pacetti, San Jose, CA (US); Syed Faiyaz Ahmed Hossainy, Fremont, CA (US); David C. Gale, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1684 days.

(21) Appl. No.: 11/117,813

(22) Filed: Apr. 29, 2005

(65) Prior Publication Data

US 2006/0246108 A1 Nov. 2, 2006

(51) Int. Cl.
*A61F 2/00* (2006.01)
*A61F 2/82* (2013.01)

(52) U.S. Cl.
USPC .............................................. 424/423

(58) Field of Classification Search
None
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 4,983,745 A * | 1/1991 | Muller et al. .................. 549/274 |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,302,693 A | 4/1994 | Stricker et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,338,822 A | 8/1994 | Gruber et al. |
| 5,346,966 A | 9/1994 | Spinu et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,700,901 A * | 12/1997 | Hurst et al. .................. 528/354 |

(Continued)

FOREIGN PATENT DOCUMENTS

| | | |
|---|---|---|
| DE | 42 24 401 | 1/1994 |
| EP | 0 301 856 | 2/1989 |

(Continued)

OTHER PUBLICATIONS

Sousa et al., Circulation 107, p. 2274-2279, 2003.*

(Continued)

*Primary Examiner* — Nissa Westerberg
(74) *Attorney, Agent, or Firm* — Squire Patton Boggs (US) LLP

(57) ABSTRACT

Implantable devices formed of or coated with a material that includes an amorphous poly(D,L-lactide) formed of a starting material such as meso-D,L-lactide are provided. The implantable device can be used for the treatment, mitigation, prevention, or inhibition of a disorder such as atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, or combinations thereof.

24 Claims, No Drawings

(56) References Cited

U.S. PATENT DOCUMENTS

| | | |
|---|---|---|
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,857,998 A | 1/1999 | Barry |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,099,563 A | 8/2000 | Zhong |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,179,817 B1 | 1/2001 | Zhong |
| 6,180,632 B1 | 1/2001 | Myers et al. |
| 6,197,051 B1 | 3/2001 | Zhong |
| 6,203,551 B1 | 3/2001 | Wu |
| 6,211,249 B1 | 4/2001 | Cohn et al. |
| 6,214,901 B1 | 4/2001 | Chudzik et al. |
| 6,231,590 B1 | 5/2001 | Slaikeu et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,469,133 B2 | 10/2002 | Baker et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossaony et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 * | 12/2003 | Hossainy et al. ............ 623/1.13 |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,669,719 B2 * | 12/2003 | Wallace et al. ............. 623/1.12 |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |

(56) References Cited

U.S. PATENT DOCUMENTS

| | | |
|---|---|---|
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,899,731 B2 | 5/2005 | Li et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0103526 A1 * | 8/2002 | Steinke ........................ 623/1.11 |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0125800 A1 | 7/2003 | Shulze et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0112170 A1 * | 5/2005 | Hossainy et al. ............. 424/423 |
| 2005/0113903 A1 | 5/2005 | Rosenthal et al. |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 184 008 | 3/2002 |
| EP | 1 192 957 | 4/2002 |
| EP | 1 273 314 | 1/2003 |
| JP | 03-103429 | 4/1991 |
| JP | 11-137694 | 5/1999 |
| JP | 2000-51367 | 2/2000 |
| JP | 2000-210377 | 8/2000 |
| JP | 2001-190687 | 7/2001 |
| JP | 2002-539854 | 9/2002 |
| JP | 2002-530389 | 11/2002 |
| SU | 872531 | 10/1981 |
| SU | 876663 | 10/1981 |
| SU | 905228 | 2/1982 |
| SU | 790725 | 2/1983 |
| SU | 1016314 | 5/1983 |

(56) References Cited

FOREIGN PATENT DOCUMENTS

| | | |
|---|---|---|
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 9856312 A1 * | 12/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/67990 | 9/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/022807 | 3/2003 |
| WO | WO 03/028780 | 4/2003 |
| WO | WO 03/037223 | 5/2003 |
| WO | WO 03/039612 | 5/2003 |
| WO | WO 03/068289 | 8/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |
| WO | WO 2004/026357 | 4/2004 |

OTHER PUBLICATIONS

Li and McCarthy, Macromolecules, 32, p. 4454-4456, 1999.*

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent*: Comparative Study of Two Drugs, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Ikada et al., *Stereocomplex Formation Between Enantiomeric Poly(lactides)*, Macromolecules 20, pp. 904-906, 1987.

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Odian, "Principles of Polymerization" 3 rd ed. A Wiley-Interscience Publication, pp. 24-28, 1991.

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Okihara et al., "Crystal Structure of Stereocomplex of Poly(L-lactide) and Poly(D-lactide)", Macromol. Sci-Phys, B30, pp. 119-140, (1991).

Ozaki et al., *New Stent Technologies, Progress in Cardiovascular Diseases*, vol. XXXIX(2):129-140 (Sep./Oct. 1996).

Ovit et al., "Stereochemistry of Lactide Polymerization with Chiral Catalysts: New Opportunities for Stereocontrol Using Polymer Exchange Mechanisms", J. Am. Chem. Soc. 124, pp. 1316-1326, 2002.

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

(56) References Cited

OTHER PUBLICATIONS

Shigeno, *Prevention of Cerebrovascular Spasm by Bosentan, Novel Endothelin Receptor*, Chemical Abstract 125:212307 (1996).

Tsuji et al., "Stereocomplex Formation between Enantiomeric Poly(lactic acid)s. 3. Calorimetric Studies on Blend Films Cast from Dilute Solution", Macromolecules, vol. 24, No. 20, pp. 5651-5656, 1991.

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

International Search Report for PCT/US2006/014889 filed Apr. 19, 2006, mailed Sep. 18, 2006, 13 pgs.

Zhang et al. "Miscibility, crystallization and morphology of poly($\beta$-hydroxybutyrate)/poly (*d,l*—lactide) blends", Polymer, vol. 37, No. 2, pp. 235-241, 1996.

Chabot et al., Configurational structures of lactic acid stereocopolymers as determined by $^{13}$C-{$^1$H} n.m.r., Polymer vol. 24, pp. 53-59 (1983).

Li et al., "Crystalline Oligomeric Stereocomplex as an Intermediate Compound in Racemic Poly(DL-Lactic Acid) Degradation", Polymer Int. 33, pp. 37-41 (1994).

Schindler, "Poly(Lactic Acid). I. Stereosequence Distribution in the Polymerization of Racemic Dilactide" Polymer Letters Ed., vol. 14, pp. 729-734 (1976).

Notice of Reasons for Rejection from JPO for Appl. No. P2008-508936, mailed Feb. 7, 2012, 3 pgs.

\* cited by examiner

AMORPHOUS POLY(D,L-LACTIDE) COATING

BACKGROUND OF THE INVENTION

1. Field of the Invention

This invention generally relates to coatings or implantable devices, such as stents or coatings on a stent, formed of a material that contains amorphous poly(D,L-lactide) (PDLLA) with a crystallinity of about or lower than 10%.

2. Description of the Background

Although stents work well mechanically, the chronic issues of restenosis and, to a lesser extent, stent thrombosis remain. Pharmacological therapy in the form of a drug-delivery stent appears a feasible means to tackle these biologically derived issues. Polymeric coatings placed onto the stent serve to act both as the drug reservoir, and to control the release of the drug. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

A current paradigm in biomaterials is the control of protein adsorption on the implant surface. Uncontrolled protein adsorption, leading to mixed layer of partially denatured proteins, is a hallmark of current biomaterials when implanted. Such a surface presents different cell binding sites from adsorbed plasma proteins such as fibrogen and immunoglobulin G. Platelets and inflammatory cells such as monocyte/macrophages and neutrophils adhere to these surfaces. Unfavorable events can be controlled by the use of non-fouling surfaces. These are materials, which absorb little or no protein, primarily due to their hydrophilic surface properties.

Another limitation of current drug-delivery stents stems from the fact that the stent is a foreign body. Use of drug-delivery stents has proved successful by use of controlled release of anti-proliferative or anti-inflammatory drugs to control restenosis. However, drug-delivery stents still have a small, but measurable, incidence of sub-acute thrombosis. Moreover, drug-delivery stents have not driven restenosis to zero levels, especially in more challenging patient subsets such as diabetics or patients with small vessels, and/or long, diffuse lesions. A biomaterials-based strategy for further improving the outcome of drug-delivery stents is by the use of biobeneficial materials or surfaces in stent coatings. A biobeneficial material is one which enhances the biocompatibility of a device by being non-fouling, hemocompatible, actively non-thrombogenic, or anti-inflammatory, all without depending on the release of a pharmaceutically active agent.

Poly(lactic acid) (PLA) is a bioabsorbable material with a long history of use. One of the negative aspects of using bioabsorbable material is late term inflammatory reactions. One of the reasons causing late term inflammatory reactions is a burst release of acidic degradation products at a late time point. Another cause is the release of polymer crystallites at a late time point once the amorphous polymer phase has degraded. It has been well documented that polymerization of D,L-lactic acid, and during degradation of the resulting polymers, can lead to the formation of stereocomplexes of PLA polymers. These stereocomplexes are the result of co-crystallization of enatiomerically pure poly(D-lactic acid) (PDLA) and poly(L-lactic acid) (PLLA) polymers or polymeric blocks (see, for example, Ikada, Y., et al., Macromolecules 20:904-06 (1987)). Studies have shown that these stereocomplexes have crystalline structures (see, for example, Okihara, T., et al., J. Macromol. Sci. Phys. B30(1/1):119-140 (1991); Tsuji, H., et al., Macromolecules 24:5651-6 (1991)). Accordingly, PLA formed by polymerization of D,L-lactic acids which allows for the formation of homologous sequences of L-lactic and/or D-lactic acid may cause late term inflammatory reactions.

The present invention addresses such problems by providing a polymeric material for coating implantable devices.

SUMMARY OF THE INVENTION

Provided herein is a coating on an implantable device. The coating contains anamorphous PLA polymer formed of D-lacic acid and L-lactic acid, the polymer is not made from a 50/50 blend of L,L-lactide and D,D-lactide. The amorphous PLA polymer has a crystallinity of about 10% or lower, about 5% or lower, about 2% or lower, about 1% or lower, about 0.5% or lower, about 0.2% or lower, about 0.1% or lower, about 0.05% or lower, about 0.01% or lower, about 0.005% or lower, or about 0.0001%. The polymer defined herein can be used alone or in combination with another biocompatible polymer and/or a biobeneficial material to form coatings on implantable medical devices, or to form the implantable medical devices themselves. In some embodiments, the coatings or medical devices optionally include a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, prodrugs thereof, co-drugs thereof, and combinations thereof. The implantable device can be implanted in a patient for the treatment, mitigation, prevention, or inhibition of a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION

Provided herein is a coating on an implantable device. The coating contains anamorphous PLA polymer formed of D-lacic acid and L-lactic acid, which is not made from a 50/50 blend of L,L-lactide and D,D-lactide. The amorphous PLA polymer has a crystallinity of about 10% or lower, about 5% or lower, about 2% or lower, about 1% or lower, about 0.5% or lower, about 0.2% or lower, about 0.1% or lower, about 0.05% or lower, about 0.01% or lower, about 0.005% or lower, or about 0.0001%. The polymer defined herein can be used alone or in combination with another biocompatible polymer and/or a biobeneficial material to form coatings on implantable medical devices, or to form the implantable medical devices themselves. In some embodiments, the coatings or medical devices optionally include a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy) ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), pimecrolimus, imatinib mesylate, midostaurin, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Polymer crystallinity is generally used to define the morphology of a polymer. Crystalline state of a material can be defined in a number of different ways, e.g., density, enthalpy or free energy change on heating, spectroscopic associations, presence of certain planes of registry in microscopy for instance. For example, in the terms of XRD (x-ray diffraction), a crystal is defined as perfect 3-D order. Perfect 3-D order means that the structure repeats in all directions so that by describing the structure locally (in a repeating 3-d unit) the entire structure can be uniquely described. In a polymer, crystallinity reflects the presence in the polymer regions of three-dimensional order consisting of identical repeating units with the same orientation. The most direct evidence comes from x-ray diffraction studies where the sample displays one or more sharp diffraction peaks, although other methods such as determination of a melting point by DSC are also used. The crystallinity of a polymer is a function of polymer structure and intermolecular forces, e.g., hydrogen-bonding or van der Waal's forces, of polymer molecules. A good discussion of crystallinity in polymer is given at Odian, George, *Principles of Polymerization*, 3rd ed., John Wiley & Sons, New York, 1991, p. 27.

Formation of Amorphous PLA

The formation of stereocomplexes requires the presence of homologous sequences of L-lactic acid and D-lactic acid. Under a given set of conditions, e.g., temperature, pressure, solvent(s), and concentration, the presence of a higher degree of homologous sequences of L-lactide and D-lactide in a PLA polymer will generally cause the PLA to have a higher tendency to form stereocomplexes, generating a PLA polymer with a higher degree of crystallinity. Accordingly, to form a PLA polymer with a low degree of crystallinity, it is desirable to reduce the degree of homologous sequences of L-lactide and D-lactide in a PLA polymer.

PDLLA polymers are generally synthesized by polymerization of D,L-lactide using stannous octoate as the catalyst. There are three types of D,L-lactide, meso-D,L-lactide, racemic D,L-lactide, and blend-D,L-lactide (Formulae I-III):

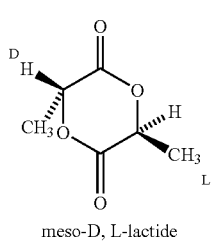

Formula I meso-D, L-lactide

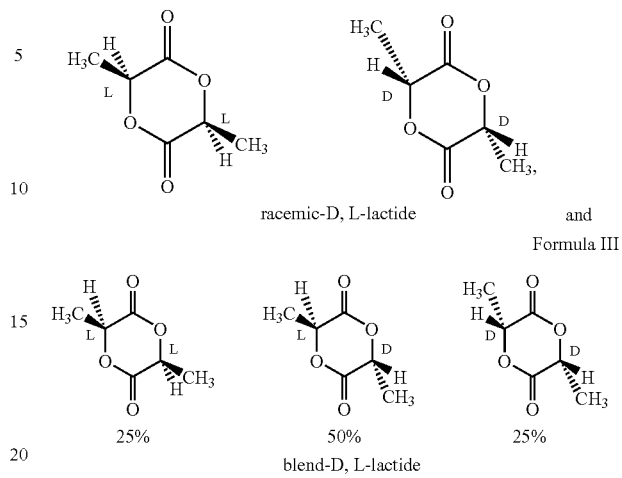

In one embodiment of the present invention, the amorphous PLA polymer can be synthesized by polymerization of a meso-lactide (Scheme I):

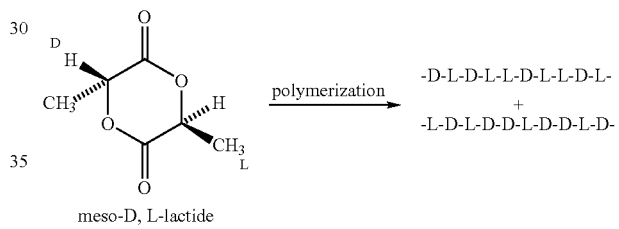

Using meso-D,L-lactide, the greatest number of Ds or Ls in sequence is 2. Consequently, there are no homologous sequences with more than 2 Ds or Ls in the polymer.

In another embodiment, the amorphous PLA polymer can be synthesized by polymerization of racemic-lactide (Scheme II):

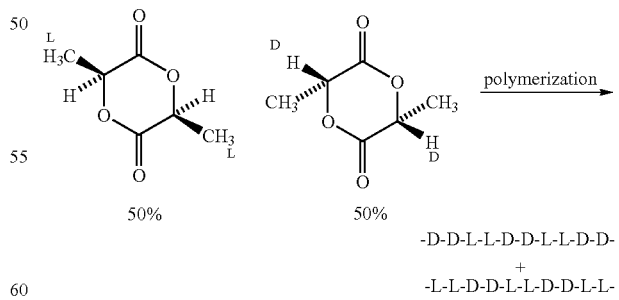

The distribution of the various combinations of D-lactide and L-lactide depends on the length of the polymer sequence, but is predictable with statistics. For example, in a sequence of eight (8) lactates, the distribution of all D or all L is given in Table 1.

TABLE 1

| Distribution of D or L lactates in a eight(8) lactate sequence | |
|---|---|
| 2 in sequence (L-L/D-D): | 12.5%, |
| 4 in sequence (L-L-L/D-D-D-D): | 50%, |
| 6 in sequence (D-D-D-D-D-D/L-L-L-L-L-L): | 25%, |
| 8 in sequence (D-D-D-D-D-D-D-D/L-L-L-L-L-L-L-L): | 12.5% |

In another embodiment of the present invention, the amorphous PLA polymer can be synthesized by polymerization of blend-D,L-lactide. According to distribution statistics, a blend of 50% D-lactide and 50% L-lactide has a distribution of 25% D,D-lactide, 50% meso-D,L-lactide, and 25% L-lactide (Formula III), which is essentially a mixture of meso-D,L-lactide and racemic-D,L-lactide. Therefore, the polymerization of blend-D,L-lactide will generate a PLA polymer having homologous sequences of lactates whose number and size in the polymer are between those of the PLA polymers from the polymerization of meso-D,L-lactide and racemic-D,L-lactide.

The D,L-lactides as used herein is cyclic lactides. Preparation of cyclic lactides are well documented in the art, and cyclic lactides are generally made by: (1) polycondensation of lactic acid to make a low MW poly(lactic acid), (2) depolymerization of the poly(lactic acid) by increasing the temperature and decreasing the pressure, and (3) distilling off the cyclic lactide formed.

meso-D,L-lactides can be isolated from the cyclic lactides made according to the procedures set forth above. The dipole moments of the D,D/L,L-lactides and the dipole moment of the meso-D,L-lactide are different. Accordingly, meso-D,L-lactide can be separated from D,D/L L-lactides by conventional separation methods such as distillation, recrystallization, and/or chromatography.

The amorphous PLA polymer can be used to form an implantable device such as a stent or a coating on an implantable device such as a stent. In some embodiments, the amorphous PLA polymer can be used alone or in combination with another biocompatible polymer, optionally with a biobeneficial material and/or a bioactive agent.

Coating Constructs

In some embodiments, the poly(meso-D,L-lactide) (meso-DLPLA) can be used to modulate absorption rate in vivo for both a coating such as a coating formed onto a drug-delivery stent and a fully absorbable device such as a stent. The meso-DLPLA composition can range from about 5% to about 100% in the coating or the absorbable device. For example, the meso-DLPLA can be used in combination with racemic-poly(D,L-lactide) (racemic-DLPLA) to form a coating having any of the following construct schemes:

(1) blends of meso-DLPLA with racemic-DLPLA,
(2) a layer of meso-DLPLA as the outer layer and a layer of racemic-DLPLA as the inner layer or vice versa to modulate the absorption rate of the coating and/or to modulate the release rate of a drug, if any, and
(3) alternating the meso-DLPLA and the racemic-DLPLA.

Alternatively, the meso-DLPLA can be used with syndiotactic polylactide (LPLA) to form a coating having any of the following construct schemes, each independently or in combination:

(1) blends of meso-DLPLA with LPLA,
(2) a layer of meso-DLPLA as the outer layer and a layer of LPLA as the inner layer or vice versa to modulate the absorption rate of the coating and/or to modulate the release rate of a drug, if any, and
(3) alternating the meso-DLPLA and the LPLA.

In some embodiments, the meso-DLPLA can form a composition with racemic-DLPLA to form a coating with LPLA having any of the following construct schemes, each independently or in combination:

(1) blends of LPLA with a composition that includes meso-DLPLA and racemic-DLPLA, and
(2) a layer that includes meso-DLPLA and racemic-DLPLA alternating with a layer that includes LPLA. The alternating structure can be applied either by coating the DLPLA or extruding.

In one embodiment, the meso-DLPLA can form a composition with poly(L-lactide-co-D,L-lactide) (LPLA-co-DLPLA) to form a coating with LPLA having any of the following construct schemes, each independently or in combination:

(1) blends of LPLA with a composition that includes meso-DLPLA and LPLA-co-DLPLA, and
(2) a layer that includes meso-DLPLA and LPLA-co-DLPLA alternating with a layer that includes LPLA.

Syndiotactic polylactide (LPLA) can be synthesized from meso-lactide by using a chiral catalyst (see, e.g., Ovit, T.M., et al., Stereochemistry of lactide polymerization with chiral catalysts: new opportunities for stereocontrol using polymer exchange mechanisms, *J Am Chem Soc.* 124(7):1316-26 (2002)).

The coating having meso-poly(D,L-lactide) can have a variety of beneficial properties. For example, inclusion of meso-poly(D,L-Lactide) increases the absorption rate of polymer matrix in the coating, and inclusion of meso-poly(D,L-Lactide) increases the water absorption of polymer matrix due to the absence of D-D-D or L-L-L blockyness in the polymer. Therefore, by varying the absorption rate and water absorption of the polymer matrix, one can modulate the release rate of a drug encapsulated within the polymer matrix. In addition, the increased absorption rate and water absorption of the polymer matrix allows the use of high MW starting material for relevant mechanical properties in certain applications.

Biocompatible Polymers other than Meso-DLPLA

In some embodiments of the present invention, the meso-DLPLA can be used in combination with one or more additional biocompatible polymer which is not meso-DLPLA. The additional biocompatible polymer can be biodegradable (both bioerodable or bioabsorbable) or nondegradable, and can be hydrophilic or hydrophobic. Hydrophilic is defined to have a $\delta$ (cal/cm)$^{1/2}$ value (Hildebrand solubility parameter) greater than about 8.5 (cal/cm)$^{1/2}$, e.g., a $\delta$ value of about 8.5(cal/cm)$^{1/2}$, about 9.5 (cal/cm)$^{1/2}$, about 10.5 (cal/cm)$^{1/2}$ or about 11.5 (cal/cm)$^{1/2}$. The Hildebrand solubility parameter is a measure of the cohesive energy density, or polarity of a substance.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly polyesters, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVD F-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, and combinations thereof. In some embodiments, the polymer can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), and poly(L-lactic acid-co-glycolic acid), respectively.

Biobeneficial Material

The meso-DLPLA can form an absorbable device, or a coating, optionally with a biobeneficial material. The combination can be mixed, blended, or coated in separate layers. The biobeneficial material useful in the coatings described herein can be a polymeric material or non-polymeric material. The biobeneficial material is preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. poly(ethylene oxide/poly(lactic acid) (PEO/PLA)), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as albumin, fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, and combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Bioactive Agents

The meso-DLPLA can form a absorbable device or a coating optionally with one or more bioactive agents. These bioactive agents can be any agent which is a therapeutic, prophylactic, or diagnostic agent. These agents can have antiproliferative or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy] ethyl-rapamycin, and 40-O-tetrazole-rapamycin. Examples of paclitaxel derivatives include docetaxel. Examples of anti-neoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, patent foramen ovale closure devices, cerebrospinal fluid shunts, pacemaker electrodes, and endocardial leads (e.g., FINE-LINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device itself, such as a stent, can also be made from the described inventive polymers or polymer blends.

Method of Use

In accordance with embodiments of the invention, a coating or device of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. In accordance with some other embodiments of the invention, bioabsorbable or non-degradable devices can be formed of a material containing the polymer of Formula I. The material can be the polymer of Formula I or a polymer blend containing the polymer of Formula I with one or more biocompatible polymers, optionally with a biobeneficial material and/or a bioactive agent, which are defined above.

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth prophetic examples. All parameters and data are not to be construed to unduly limit the scope of the embodiments of the invention.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

Example 1

Synthesis of meso-poly(D,L-lactide)

To a 500 ml, 3-necked flask equipped with argon purge, vacuum line, short-path distillation head, and mechanical stirrer is added L-lactic acid (125 g, y mole), D-lactic acid (125 g, y, mole), and zinc oxide (5 g. Y mole). A vacuum of 100 mm Hg is applied, and the solution is heated with stirring at 140° C. for about 8 hours to form lactic acid oligomer while distilling off the water formed. The pressure is lowered to 2 mm Hg, and the solution temperature raised to about 210° C. to distill off the lactide formed by depolymerization, which consists of a 25/25/50 blend of L-lactide, D-lactide, and meso-D,L-lactide. The lactides formed are transferred to another 500 ml flask, and vacuum distilled at a pressure of 1 mm Hg to separate the racemic-D,L-lactide from the meso-D,L-lactide. The meso-BD,L-lactide can also be separated form the racemic-D,L-lactide by recrystallization. In general, the racemic-D,L-lactide will crystallize more readily, leaving the meso-D,L-lactide in the mother liquor.

Example 2

Synthesis of poly(meso-D,L-lactide)

To a 250 ml, three necked flask, equipped with magnetic stirring, vacuum, and argon purge is added 1,6-hexanediol (14.77 g, 0.125 mole). Using an oil bath, the diol is heated to 60° C., and stirred under vacuum for two hours to remove water. The flask is purged with argon and the meso-D,L-lactide from Example 1 (108.0 g, 0.75 mole) is added. Vacuum is applied with stirring for another 30 minutes. After purging with argon, the flask is heated to 140° C., and polymerization initiated by addition of 10.8 ml of a 5% (w/w) solution of stannous octoate in dry toluene. After stirring for 24 hours, the reaction solution is cooled and poured into 500 ml of cold methanol to precipitate the polymer. The polymer is washed with methanol/petroleum ether and dried under vacuum.

Example 3

Stent Coating with poly(meso-D,L-lactide)

A medical article with two layers of coating can be fabricated to comprise everolimus by preparing a first composition and a second composition, wherein the first composition can be a primer layer comprising a matrix of a polylactide, and the second composition can be a matrix of a polylactide and an active agent. A first composition can be prepared by mixing the poly(meso-D,L-lactide) at 2% solids (w/w) in a 70/30 (w/w) blend of acetone/cyclohexanone. The first composition can be sprayed onto a surface of a bare 12 mm VISION™ stent (Guidant Corp.) ("example stent"), and dried to form a primer. An example coating technique comprises spray-coating with a 0.014 round nozzle, a feed pressure of about 0.2 atm and an atomization pressure of about 1.3 atm, applying about 20 μg of wet coating per pass until a wet coating weight of about 80 μg is reached, drying the coating at about 50° C. for about 10 seconds between passes and baking the coating at about 80° C. for about 1 hour after the final pass to form a dry primer layer with about 60 μg of solids. A second composition can be prepared by mixing poly(meso-D,L-lactide) with everolimus at a weight ratio of 1/2 with 2% (w/w) polymer solids in a 70/30 acetone/cyclohexanone blend. This solution is sprayed onto the primered stents and dried to form an agent layer coating. Spray-coating is performed with a 0.014 nozzle, a feed pressure of about 0.2 atm and an atomization pressure of about 1.3 atm, applying about 20 μg of wet coating per pass until a weight coating weight of about 190 μg is reached, drying the coating at about 50° C. for about 10 seconds between passes and baking the coating at about 50° C. for about 1 hour after the final pass to form a dry agent layer with about 167 μg of solids.

What is claimed is:

1. A coating comprising an amorphous poly(D,L-lactide) (PDLLA) having a degree of crystallinity of 10% or below and an additional biocompatible polymer,
    wherein the PDLLA is not made from a 50/50 blend of L,L-lactide and D,D-lactide,
    wherein the amorphous PDLLA is poly(meso-D,L-lactide) (meso-DLPLA), racemic poly(D,L-lactide) (racemic-DLPLA), or combination thereof,
    wherein the coating further comprises a syndiotactic polylactide (LPLA),
    and wherein the additional biocompatible polymer is selected from the group consisting of polymers and copolymers of 3-hydroxypropanoate, 3-hydroxyhexanoate, 3-hydroxyheptanoate, 3-hydroxyoctanoate, 4-hydroxyhexanote, 4-hydroxyheptanoate, and 4-hydroxyoctanoate; poly(tyrosine carbonates); poly(tyrosine ester); polyphosphoester; polyphosphoester urethane; polycyanoacrylates; poly(vinylidene fluoride-co-hexafluoropropylene); cellulose butyrate; phosphoryl choline; poly(aspirin); polymers and co-polymers of alkoxymethacrylate, alkoxyacrylate, and 3-trimethylsilylpropyl methacrylate (TMSPMA); poly(styrene-isoprene-styrene)-PEG (SIS-PEG); polystyrene-PEG; polyisobutylene-PEG; polycaprolactone-PEG (PCL- PEG); poly(methyl methacrylate)-PEG (PMMA-PEG); polydimethylsiloxane-co-PEG (PDMS-PEG); polypropylene oxide-co-polyethylene glycol; poly(tetramethylene glycol); hydroxy functional poly(vinyl pyrrolidone); and combinations thereof.

2. The coating of claim 1, wherein the amorphous PDLLA has a degree of crystallinity of about or below 1%.

3. The coating of claim 1, wherein the additional biocompatible polymer is biodegradable.

4. A stent comprising the coating of claim 1.

5. A stent comprising the coating of claim 3.

6. A stent comprising the coating of claim 2.

7. The stent of claim 4, wherein the coating further comprises a biobeneficial material, and
wherein the additional biocompatible polymer is biodegradable.

8. The stent of claim 7, wherein the biobeneficial material is selected from the group consisting of poly(ethylene glycol), poly(alkylene oxides), phosphoryl choline, 2-methacyloyloxyethylphosphoryl choline, poly(vinyl pyrrolidone), poly(styrene sulfonate), NO-donor polymers, hyaluronic acid, fibrin, albumin, elastin, dextran, dextrin, polysaccharides, heparin, fullerenes, and a combination thereof.

9. The stent of claim 4, further comprising a bioactive agent.

10. The stent of claim 5, further comprising a bioactive agent.

11. The stent of claim 9, wherein the bioactive agent is selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy) ethoxy]ethyl-rapamycin, and 40-O-tetrazole-rapamycin, ABT-578, pimecrolimus, imatinib mesylate, midostaurin, clobetasol, and a combination thereof.

12. The stent of claim 10, wherein the bioactive agent is selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy) ethoxy]ethyl-rapamycin, and 40-O-tetrazole-rapamycin, ABT-578, pimecrolimus, imatinib mesylate, midostaurin, clobetasol, and a combination thereof.

13. An absorbable stent formed of a material comprising an amorphous poly(D,L-lactide) (PDLLA) having a degree of crystallinity of about or below 10% and an additional biocompatible polymer,
wherein the PDLLA is not made from a 50/50 blend of L,L-lactide and D,D-lactide,
wherein the amorphous PDLLA is poly(meso-D,L-lactide) (meso-DLPLA), racemic poly(D,L-lactide) (racemic-DLPLA), or combination thereof,
wherein the material further comprises a syndiotactic polylactide (LPLA), and
wherein the additional biocompatible polymer is selected from the group consisting of polymers and copolymers of 3-hydroxypropanoate, 3-hydroxyhexanoate, 3-hydroxyheptanoate, 3-hydroxyoctanoate, 4-hydroxyhexanote, 4-hydroxyheptanoate, and 4-hydroxyoctanoate; poly(tyrosine carbonates); poly(tyrosine ester); polyphosphoester; polyphosphoester urethane; polycyanoacrylates; poly(vinylidene fluoride-co-hexafluoropropylene); cellulose butyrate; phosphoryl choline; poly(aspirin); polymers and co-polymers of alkoxymethacrylate, alkoxyacrylate, and 3-trimethylsilylpropyl methacrylate (TMSPMA); poly(styrene-isoprene-styrene)-PEG (SIS-PEG); polystyrene-PEG; polyisobutylene-PEG; polycaprolactone-PEG (PCL-PEG); poly(methyl methacrylate)-PEG (PMMA-PEG); polydimethylsiloxane-co-PEG (PDMS-PEG); polypropylene oxide-co-polyethylene glycol; poly(tetramethylene glycol); hydroxy functional poly(vinyl pyrrolidone); and combinations thereof.

14. The absorbable stent of claim 13, further comprising a biobeneficial material and/or a bioactive agent.

15. The absorbable stent of claim 13, further comprising a biobeneficial material and a bioactive agent.

16. A method of treatment of a disorder in a patient comprising implanting in the patient a stent of claim 9, wherein the disorder is selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

17. A method of treating a disorder in a patient comprising implanting in the patient an absorbable stent of claim 13, wherein the disorder is selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

18. An implantable device comprising a coating that comprises:
alternating layers comprising meso-DLPLA and comprising racemic-DLPLA; wherein one layer is a primer layer consisting of meso-DLPLA and a syndiotactic polylactide (LPLA).

19. An implantable device comprising a coating that comprises:
alternating layers comprising meso-DLPLA and comprising syndiotactic polylactide (LPLA); wherein one layer is a primer layer consisting of meso-DLPLA and a syndiotactic polylactide (LPLA).

20. The coating of claim 3, wherein the additional biocompatible polymer is selected from the group consisting of poly(vinylidene fluoride-co-hexafluoropropylene); phosphoryl choline; poly(tetramethylene glycol); and combinations thereof.

21. The stent of claim 7, wherein the biobeneficial material is selected from the group consisting of albumin, a block copolymer having poly(ethylene glycol) and poly(butylene terephthalate) blocks, and combinations thereof.

22. The coating of claim 1, wherein the additional biocompatible polymer is selected from the group consisting of polymers and copolymers of 3-hydroxypropanoate, 3-hydroxyhexanoate, 3-hydroxyheptanoate, 3-hydroxyoctanoate, 4-hydroxyhexanote, 4-hydroxyheptanoate, and 4-hydroxyoctanoate; poly(tyrosine carbonates); polyphosphoester; polycyanoacrylates; poly(vinylidene fluoride-co-hexafluoropropylene); cellulose butyrate; phosphoryl choline; poly(aspirin); polymers and co-polymers of alkoxymethacrylate, alkoxyacrylate, and 3-trimethylsilylpropyl methacrylate (TMSPMA); poly(styrene-isoprene-styrene)-PEG (SIS-PEG); polystyrene-PEG; polyisobutylene-PEG; polycaprolactone-PEG (PCL-PEG); poly(methyl methacrylate)-PEG (PMMA-PEG); and combinations thereof.

23. The stent of claim 4, wherein the additional biocompatible polymer is selected from the group consisting of polymers and copolymers of 3-hydroxypropanoate, 3-hydroxyhexanoate, 3-hydroxyheptanoate, 3-hydroxyoctanoate, 4-hydroxyhexanote, 4-hydroxyheptanoate, and 4-hydroxyoctanoate; poly(tyrosine carbonates); polyphosphoester; polycyanoacrylates; poly(vinylidene fluoride-co-hexafluoropropylene); cellulose butyrate; phosphoryl choline; poly(aspirin); polymers and co-polymers of alkoxymethacrylate, alkoxyacrylate, and 3-trimethylsilylpropyl methacrylate (TMSPMA); poly(styrene-isoprene-styrene)-PEG (SIS-PEG); polystyrene-PEG; polyisobutylene-PEG; polycaprolactone-PEG (PCL-PEG); poly(methyl methacrylate)-PEG (PMMA-PEG); and combinations thereof.

24. The stent of claim 21, wherein the biobeneficial material is a block copolymer having poly(ethylene glycol) and poly(butylene terephthalate) blocks.

\* \* \* \* \*

UNITED STATES PATENT AND TRADEMARK OFFICE
CERTIFICATE OF CORRECTION

PATENT NO.        : 8,778,375 B2
APPLICATION NO.   : 11/117813
DATED             : July 15, 2014
INVENTOR(S)       : Pacetti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1815 days.

Signed and Sealed this
Eighth Day of September, 2015

Michelle K. Lee
*Director of the United States Patent and Trademark Office*